United States Patent [19]

Hodgin

[11] Patent Number: 4,616,036

[45] Date of Patent: Oct. 7, 1986

[54] FORMULATION FOR THE CONTROL OF NEMATODES

[76] Inventor: Byron Hodgin, 631 White Pine Tree Rd., Venice, Fla. 33595

[21] Appl. No.: 775,415

[22] Filed: Sep. 12, 1985

[51] Int. Cl.[4] ........................ A01N 33/18; A01N 33/24
[52] U.S. Cl. .................................................. 514/470
[58] Field of Search ........................................ 514/740

[56] References Cited

U.S. PATENT DOCUMENTS

| | | | |
|---|---|---|---|
| 1,983,546 | 12/1934 | Johnson | 514/740 |
| 2,864,735 | 12/1958 | Stansbury et al. | 514/740 |
| 3,911,121 | 10/1975 | Roberts | 514/120 |

FOREIGN PATENT DOCUMENTS

| | | | |
|---|---|---|---|
| 46-35874 | 10/1971 | Japan | 514/740 |

OTHER PUBLICATIONS

Chem. Abst. 68:2192s (1968)–Reber.
Chem. Abst. 70:10579e (1969)–Mankau.
Chem. Abst. 74:110790e (1971)–Maggenti et al.
Chem. Abst. 74:123989q (1971)–Jones et al.
Chem. Abst. 76:42716n (1972)–Eissa.
Chem. Abst. 90:17691g (1979)–Tsujigaito et al.
Chem. Abst. 90:163350m (1979)–Tsujigaito et al.

*Primary Examiner*—Douglas W. Robinson
*Attorney, Agent, or Firm*—George B. Oujevolk

[57] ABSTRACT

In the control of nematodes, use is made of a formulation using D-limonene as a solvent to carry an effective dosage of chloropicrin. The formulation can also include an amount of methyl isothiocyanate corresponding in volume approximately to the amount of chloropicrin. The combination of these two components is synergistic. With the further addition of diazinon, a double synergistic effect is obtained.

2 Claims, No Drawings

FORMULATION FOR THE CONTROL OF NEMATODES

BACKGROUND OF THE INVENTION

The present invention is directed to the control of undesirable soil components, and more particularly to the control of nematodes, symphylans wireworms, soil borne diseases, and weed seeds in crop land and ornamental gardens as well as commercial turf. Also included in the undesirable components are mole crickets.

BRIEF REVIEW OF THE PRIOR ART

Nematodes are a good example of undesirable soil components. Nematodes are microscopic eel worms and come in many varities. The dog hookworm is a nematode, i.e., it forms part of the animal parasitic group. But, there are also those forming part of the plant parasitic group. These plant parasitic components feed on plant roots and poisons the plant. They also cause damage to the mammals, including humans who eat the plants. These undesirable soil components have been controled by the injection into the soil of various formulations, one component suggested has been chloropicrin, but this component is very expensive and has not proven too effective, when carried out in practice. The use of chloropicrin has been suggested by Kirk et al, "Encyclopedia of Chemical Technology" in its several editions in the article on Chloropicrin. Nevertheless, in practice, chloropicrin or $Cl_3CNO_2$ is not now used in the various commercially avilable formulations except as a warning agent for other fumigants.

Further inhibiting the use of chloropicrin is the tendency of chloropicrin to contaminate such items as beer and soda cans as described in the case of BURKE PEST CONTROL, INC. v. JOSEPH SCHLITZ BREWING COMPANY, 438 So. 2d 95 (Fla. App. 2 Dist. 1983), wherein the brewing company discovered that after a fumigation treatment, from ten to sixty-six nanograms of chloropicrin remained on the can liners which contaminated the cans and made them useless.

Now it has been discovered that the undesirable effects of chloropicrin can be minimized and eliminated by using D-limonene (also called dl-limonene) as a solvent. D-limonene is a material of the terpene family. The terpene family has been most bountiful in providing the means to produce synthetic rubber and other valuable discoveries because of isoprene and the isoprene rule wherein carbon skeletons made of isoprene units are joined in a regular head-to-tail way, repeating the double bonds between molecules or other chemical particles. However, dl-limonene (the "dl" signifying dextro-levo) is a solvent and as such usually does not enhance chemical reaction.

The present invention contemplates the use of D-limonene as a synergistic solvent in connection with the use of agricultural chemicals. Thus, it has now been discovered that a formulation can be provided for the control of nematodes and similar undesirable soil components where the formulation makes use of D-limonene as a solvent for the chloropicrin. Additionally, methyl isothiocyanate can be included in the formulation. Effective amounts of diazinon, if also added will provide a double synergistic effect, the first synergistic effect being the combination of the chloropicrin and D-limonene and the second synergistic effect will be the addition of diazinon.

SUMMARY OF THE INVENTION

Generally speaking the present invention contemplates the following formulations, the amounts being of the order of the quantities shown in parts by weight:

| Formulation I | Formulation II | Formulation III | Formulation IV |
|---|---|---|---|
| 83% D-limonene | 70% D-Limonene | 73% D-limonene | 65% D-Limonene |
| 17% Chloropicrin | 18% Chloropicrin | 14.5% Chloropicrin | 13% Chloropicrin |
| | 14% Methyl Isothiocyanate | 12.5% Diazinon | 10% Methyl Isothiocyanate |
| | | 12% Diazinon | |

DETAILED DESCRIPTION

As used herein, the terms hereinafter listed have the meanings shown next to the particular term:

D-limonene is 4-isopropenyl-1-methyl-1-cyclohexene. The structural formula is:

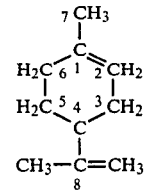

methyl isothiocyanate is $CH_2SCN$, being a member of the isocyanate family having the formula R—SCN, where "R" is a hydrocarbon radical Diazinon is the trade name for phosphorothioic acid. The structural formula is:

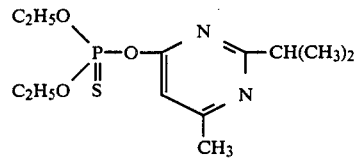

chloropicrin has the formula $Cl_3CNO_2$ and is otherwise known as trichloronitromethane T is Telone, a Dow Chemical Co. product which is dichloropropene and has the formula:

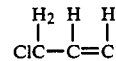

C-17 is also known as Soilex is 17% Chloropicrin, 83% D-limonene

C-50 is 50 % chloropicrin, 50% D-limonene

Telone II is 92% dichloropropene

C-17-S is C-17 in a diazinon solution

Vorlex is Telone II plus 20% methyl isothiocyanate

In carrying the invention into practice, various formulations were prepared having about 5 parts by weight and about 80 parts by weight of D-limonene as a solvent into which was added between about 10 parts by weight and about 90 parts by weight chloropicrin, namely, $Cl_3CNO_2$, additionally, in some of the formulations there was added about 80 parts by weight to about 20 parts by weight of methyl isothiocyanate. As a further formulation, several batches were prepared containing only D-limonene and methyl isothiocyanate, namely 10 parts by weight to about 50 parts by weight of the methyl isothiocyanate to about 50 parts by weight to about 90 parts by weight of the D-limonene solvent. Also, in some batches diazinon was added in quantities of from zero to about 20 parts by weight.

For the purpose of giving those skilled in the art a better understanding of the invention, the following illustrative examples are given:

Formulations prepared by the applicant herein were tested against formulations of the prior art at several locations in connection with various crops as shown:

(I) Location: Gainesville, Fla., University of Florida Institute of Food and Agricultural Sciences.
Crop: Peanuts; Time August/October 1984
Formulations:
  (1) C-17 (hereinbefore described) "SOILEX"
  (2) Telone II 1-3-dichloropropane
  (3) Vorlex, 1-3-dichloropropane+20% methyl isothiocyonate The formulation used, namely 17% chloropicrin and 83% D-limonene had a specific gravity of 0.961 or approximately 8 Lbs. per gallon, a boiling point of 112° C., a freezing point of −81° C., a flash point greater than 130° F., vapor pressure at 20° C. of −17 mm Hg. It is almost insoluble in water, soluble in alcohol, petroleum solvents, chlorinated solvents and carbon disulfide. In the presence of water, it becomes corrosive to steel, aluminum, magnesium alloys and vinyl plastics.

(II) Location: Boca Raton, Fla., Boca West Golf Course.
Time: April, 1985
Formulations:
  (1) T, Telone (hereinbefore described)
  (2) C-17 (hereinbefore described)
  (3) C-17-S (hereinbefore described)
  (4) C-50 (hereinbefore described)
  (5) C-17-D is C-17 as hereinbefore described plus technical DIAZINON (92%)

(III) Location: Tifton, Ga., Costal Plain Experiment Station, Donald Benson Farm, Tift County, Ga.
Crop: Peanuts; Time May/September 1984
Formulations:
  (1) T, Telone II
  (2) Vorlex
  (3) C-17, Soilex
  (4) Nemacur Conclusion, in all the aforementioned tests the formulations described herein namely, D-limonene as a solvent with an effective amount of chloropicrin, and, also by adding an effective amount of methyl-isothiocyanate, and/or with an effective amount of phosphorothioc acid were superior and usually vastly superior to the other formulations shown of the prior art. In the formulations tested, the D-lomonene solvent consist of between about 5 to about 80 parts by weight and the chloropicrin may consist of between about 10 and about 90 parts by weight, the methyl-isothiocyanate component may be from about 20 to about 80 parts by weight, and may include between about zero to about 20 parts by weight of phosphorothioc acid. Another formulation which is effective consists of about 10 to about 50 parts by weight of methyl-isothiocyanate mixed into about 50 to about 90 parts by weight of D-limonene solvent. The combination of chloropicrin and methyl isothiocyanate is synergistic. With the further addition of diazinon, a double synergistic effect is obtained.

EVALUATION OF NEMATICIDES FOR MANAGING THE PEANUT ROOT-KNOT NEMATODE ON PEANUT, 1984:

| Treatment and overall rate per acre (active)$^X$ | Methods of application & rate per 100 l. ft. row | Yield lb/acre | % Damage | % SMK$^Y$ | Value/ acre | No. nematodes/250 cm$^3$ soil ||||
|---|---|---|---|---|---|---|---|---|---|
| | | | | | | Meloidogyne arenaria || Criconemella curvatum ||
| | | | | | | Aug 10 | Oct 9 | Aug 10 | Oct 9 |
| Telone II 15.0 gal | 7 days preplant, 2-chisels, 10 inches apart; 65 ml | 3,365a$^Z$ | 2 | 70 | $971 | 4b | 191de | 86bcdefg | 328bcdef |
| Telone II 15.0 gal | 14 days preplant, 2-chisels 10 inches apart; 65 ml | 3,332ab | 3 | 69 | 944 | 10ab | 211de | 76bcdefg | 276cdef |
| Vorlex 12.0 gal | 14 days preplant, 2-chisels, 8 inches apart$^{ZZ}$; 52 ml | 3,174abc | 3 | 69 | 917 | 5ab | 793ab | 15fg | 138f |
| Telone II 12.0 gal + Temik 15 G 6.0 lb | 14 days preplant, 2-chisels, 10 inches apart + at-peg, 14 inch band; 52 ml + 49 g | 2,973abcd | 1 | 74 | 884 | 30ab | 110e | 103bcdef | 454abc |
| Vorlex 12.0 gal + Furadan 15 G 6.0 lb | 14 days preplant, 2-chisels, 8 inches apart$^{ZZ}$ + at-peg 14 inch band; 52 ml + 49 g | 2,919abcd | 2 | 74 | 863 | 2b | 864a | 5g | 150ef |
| Telone II 6.0 gal | 14 days preplant, 2-chisels, 10 inches apart; 26 ml | 2,842abcd | 2 | 71 | 832 | 38ab | 246cde | 140abc | 196def |
| Chloropicrin 6.0 gal | 14 days preplant, 2-chisels, 10 inches apart; 26 ml | 2,842abcd | 1 | 73 | 850 | 4b | 486bcde | 67bcdefg | 453abc |
| Untreated Control | 2-chisels, 8 inches apart | 2,793abcd | 1 | 61 | 829 | 15ab | 620abc | 78bcdefg | 346abcde |
| Untreated Control | 2-chisels, 10 inches apart | 2,766abcd | 3 | 64 | 776 | 17ab | 367cde | 132abcd | 531a |
| Telone II 12.0 gal | 14 days preplant, | 2,717abcd | 3 | 69 | 784 | 19ab | 307cde | 70bcdefg | 512ab |

-continued
EVALUATION OF NEMATICIDES FOR MANAGING THE PEANUT ROOT-KNOT NEMATODE ON PEANUT, 1984:

| | | | | | | | | | |
|---|---|---|---|---|---|---|---|---|---|
| Telone II 12.0 gal + Furadan 15 G 6.0 lb | 2-chisels, 10 inches apart; 52 ml 14 days preplant, 2-chisels, 10 inches apart + at-peg, 14 inch band; 52 ml + 49 g | 2,690abcde | 3 | 69 | 768 | 15ab | 229cde | 112bcde | 378abcd |
| Chloropicrin 3.0 gal | 14 days preplant, 2-chisels, 10 inches apart; 13 ml | 2,624abcde | 1 | 72 | 755 | 9ab | 352cde | 59cdefg | 263cdef |
| Chloropicrin 9.0 gal | 14 days preplant, 2-chisels, 10 inches apart; 39 ml | 2,467bcde | 5 | 55 | 682 | 43a | 752ab | 78bcdefg | 254def |
| Telone II 9.0 gal | 14 days preplant, 2-chisels, 10 inches apart; 39 ml | 2,467bcde | 8 | 65 | 688 | 26ab | 337cde | 193a | 458abc |
| Busan 1020 30.0 gal | 14 days preplant, 2-chisels, 8 inches apart; 130 ml | 2,412cde | 5 | 68 | 679 | 16ab | 576abcd | 40efg | 193def |
| Busan 1020 36.0 gal | 14 days preplant, 2-chisels, 8 inches apart; 156 ml | 2,292de | 5 | 71 | 662 | 37ab | 465bcde | 47defg | 207def |
| Soilex C-17 15.0 gal | 14 days preplant, 2-chisels, 10 inches apart; 65 ml | 2,129de | 6 | 52 | 578 | 10ab | 422bcde | 148ab | 382abcd |
| Telone II 15.0 gal | at-plant, 2-chisels, 10 inches apart; 65 ml | 1,851e | 3 | 64 | 503 | 6ab | 152e | 50defg | 502ab |

Peanut (*Arachis hypogaea* 'Florunner')
Root-knot nematode; *Meloidogyne arenaria*
Ring nematode; *Criconemella curvatum*
D. W. Dickson and T. E. Hewlett Dept. Of Entomology & Nematology University of Florida Gainesville, Florida 32611
[x]Rates calculated for row treatments were reduced from the overall (broadcast) dosage in proportion to the actual area tested. All dosages were calculated based on a 36 inch row
[y]Sound mature kernels based on government grading system.
[z]Means with the same letter are not significantly different according to Duncan's new multiple range test (P = 0.05).
[zz]Ridged with diskhillers.

BOCA WEST TEST PLOTS
BELONOLAIMUS ONLY
PRE-TEST, 11 DAYS, & 34 DAYS AFTER INJECTION

| | SAMPLE NUMBER | | | | | | | | | |
|---|---|---|---|---|---|---|---|---|---|---|
| NEMATODE | #1 CHECK | #2 TELONE | #3 C-17 + SAROLEX | #4 C-17 | #5 C-17 + SAROLEX | #6 C-17 + DIAZINON | #7 TELONE | #8 C-50 | #9 C-17 | #10 TELONE |
| STING-BELO-NOLAIMUS PRETEST | 32 | 32 | 24 | 12 | 48 | 52 | 68 | 24 | 60 | 72 |
| 11 DAYS | 24 | 4 | 20 | 8 | 8 | 12 | 4 | 12 | 4 | 16 |
| 34 DAYS | 52 | 8 | 24 | 8 | 4 | 24 | 28 | 8 | 36 | |
| ROOT RESPONSE @ 11 DAYS | NONE | 4 new root 1¼" long | NONE | 15 new root 3" long | 4 new root 1" long | 4 new 4" long | 11 new 3" long | NONE | 4 new 1" long | 6 new 1½" long |
| VISUAL RESPONSE @ 102 DAYS | POOR | GOOD 5' of turf | POOR | POOR | POOR | GOOD 6' of turf | GOOD 8' of turf | POOR | POOR | GOOD 6' of turf |

| | | SAMPLE NUMBER | | | | | | | |
|---|---|---|---|---|---|---|---|---|---|
| | NEMATODE | #11 C-17 + DIAZINON | #12 CHECK | #13 C-50 | #14 C-17 + DIAZINON | #15 C-50 | #16 C-17 | #17 C-17 + SAROLEX | #18 CHECK |
| | STING-BELO-NOLAIMUS PRETEST | 32 | 36 | 36 | 36 | 12 | 16 | 80 | 48 |
| | 11 DAYS | 0 | 48 | 12 | 8 | 16 | 16 | 56 | 28 |
| | 34 DAYS | 16 | 4 | 12 | 0 | 0 | 8 | 44 | 84 |
| | ROOT RESPONSE @ 11 days | NONE | NONE | NONE | NONE | 6 new 3" long | 5 new 2" long | NONE | NONE |
| | VISUAL RESPONSE @ 102 days | GOOD 8' | POOR | GOOD 5' | GOOD 20' | POOR | POOR | POOR | POOR |

| | NEMATODE Three Plot Average Below | | | | | | |
|---|---|---|---|---|---|---|---|
| | | CHECK | TELONE | C-17 + S | C-17 | C-17 + D | C-50 |
| PRETEST | | 39 | 57 | 51 | 29 | 40 | 24 |
| 11 DAYS | | 33  15%↓ | 8  86%↓ | 28  45%↓ | 9  69%↓ | 7  83%↓ | 13  46%↓ |

-continued

BOCA WEST TEST PLOTS
BELONOLAIMUS ONLY
PRE-TEST, 11 DAYS, & 34 DAYS AFTER INJECTION

| | | | | | | | | | | | | |
|---|---|---|---|---|---|---|---|---|---|---|---|---|
| 34 DAYS | 47 | 21% ↑ | 25 | 56% ↓ | 24 | 53% ↓ | 17 | 41% ↓ | 13 | 68% ↓ | 7 | 71% ↓ |

When the number of nematodes are estimated the following symbols are used:
VL—very light infestation;
L—light infestation;
MM—moderate infestation;
H—heavy infestation;
VH—very heavy infestation.

Experiment No. and Title: P5-84. Comparison of Soilex and Telone II applied to peanut 8 days preplant.
Work Unit/Project No.: 7702-20270-001
Address: Coastal Plain Experiment Station, Tifton, GA 31793
Investigator(s): Norman A. Minton and A. S. Csinos
Experiment Location: Donald Benson Farm, Tift, County
Type Experiment: Field
Nematode species: *Meloidogyne arenaria, Criconemella ornata*
Other Organisms:
Plant species and varieties: *Arachis hypogaea*, Florunner
Experimental design: Strip
Plot size and No. reps.: 2 rows, 25 ft long, 4 replications.
Soil type: Ocilla loamy soil
Soil moisture: 10.7%, May 2 when chemicals applied
Soil temperature: Maximum, 84 F., minimum, 73 F. at 4" depth when chemicals applied.
Planting dates: May 10
Treatment dates: May 2
Harvest dates: September 24
Weather conditions: Adequate rainfall for good yields
Unusual circumstances:
Progress: See Table P5A-84.

Experiment No. and Title: P6-84. Fumigant nematicides: Methods of application to peanut 8 days preplant.
Work Unit/Project No.: 7702-20270-001
Address: Coastal Plain Experiment Station, Tifton, GA 31793
Investigator(s): Norman A. Minton and A. S. Csinos
Experiment Location: Donald Benson Farm, Tift County
Type Experiment: Field
Nematode species: *Meloidogyne arenaria, Criconemella ornata*
Other Organisms:
Plant species and varieties: *Arachis hypogaea*, Florunner
Experimental design: Strip
Plot size and No. reps.: 2 rows, 25 ft long, 4 replications
Soil type: Ocilla loamy soil
Soil moisture: 10.7% May 2 when fumigant nematicides applied.
Soil temperature: Maximum, 84 F.; minimum, 73 F. at 4" depth when the chemicals applied.
Planting dates: May 10
Treatment dates: Fumigants, May 2; Nemacur, May 10
Harvest dates: September 24
Weather conditions: Adequate rainfall for good yields
Unusual circumstances:
Progress: See Table P6-84.

TABLE P5A-84

Effects of soilex and Telone II applied with the moldboard plow on peanut production, 1984.[1]

| Treatment and rate (lb ai/A) | Method of[2] application | Yield (lb/A) | % SMK[3] | Root-knot index[4] | White mold hits[5] | Stand (5/21)[6] | Vigor rating (6/22)[7] | Number nematodes/ 150 cm³ soil, 9/14/84 | |
|---|---|---|---|---|---|---|---|---|---|
| | | | | | | | | Criconemella ornata | Meloidogyne arenaria |
| Telone II 55.8 | A | 4857 ab | 80.0 | 3.1 a | 3.3 a | 12.0 a | 3.5 b | 2425 a | 530.0 a |
| Soilex 117.6 | A | 5162 a | 79.7 | 3.9 a | 3.3 a | 12.0 a | 4.3 ab | 1545 a | 422.5 a |
| Control | | 4552 b | 78.7 | 5.9 a | 4.8 a | 13.3 a | 4.5 a | 2052 a | 1475.0 a |

[1]Data within same column followed by the same letter are not significantly different (P = 0.05) according to Duncan's multiple-range test.
[2]Applied in moldboard plow furrow 10" deep on 8" centers 8 days before planting.
[3]% sound mature kernel (SMK) determined from composit sample from four replications.
[4]Root-knot index based on rating of 0–10: 0 = no galling, 10 = 100% of roots and pods galled.
[5]White mold hits = number of hits per 50 ft row. One or more plants infected per ft of row in one hit.
[6]Stand = number of plants emerged per m of row.
[7]Vigor rating based on scale of 1–5: 1 = poor growth, 5 = excellent growth.

TABLE P6A-84

Effects of three fumigant nematicides applied with moldboard plow and single chisel on peanut production, 1984.[1]

| Treatment and rate (lb ai/A) | Method of[2] application | Yield (lb/A) | % SMK[3] | Root-knot index[4] | White mold hits[5] | Stand (5/21)[6] | Vigor rating (6/22)[7] | Number nematodes/ 150 cm³ soil, 9/14/84 | |
|---|---|---|---|---|---|---|---|---|---|
| | | | | | | | | Criconemella ornata | Meloidogyne arenaria |
| Telone II 37.2 | A | 4640 ab | 76.7 | 4.3 bc | 3.0 b | 12.4 a | 2.5 bc | 3097 a | 932.5 b |
| Vorlex 38.4 | A | 2975 c | 74.0 | 9.5 a | 18.0 a | 13.3 a | 2.3 c | 1652 bc | 2297.5 a |
| Telone II 37.2 | B | 4852 ab | 79.7 | 2.9 cd | 3.3 b | 11.6 a | 3.5 a | 2782 ab | 435.0 b |
| Vorlex 38.4 | B | 4360 b | 76.0 | 3.4 cd | 3.8 b | 11.9 a | 3.0 a–c | 1702 a–c | 522.5 b |

TABLE P6A-84-continued

Effects of three fumigant nematicides applied with moldboard plow and single chisel on peanut production, 1984.[1]

| Treatment and rate (lb ai/A) | Method of[2] application | Yield (lb/A) | % SMK[3] | Root-knot index[4] | White mold hits[5] | Stand (5/21)[6] | Vigor rating (6/22)[7] | Number nematodes/ 150 cm³ soil, 9/14/84 | |
|---|---|---|---|---|---|---|---|---|---|
| | | | | | | | | Crico- nemella ornata | Meloido- gyne arenaria |
| Soilex CP 39.2 | B | 4476 b | 78.3 | 4.1 bc | 3.0 b | 11.3 a | 3.0 a–c | 2597 ab | 700.0 b |
| Nemacur 15 G 2.5 | C | 5064 a | 78.7 | 1.4 d | 3.3 b | 11.6 a | 3.3 ab | 667 c | 470.0 b |
| Control | | 4325 b | 77.0 | 6.2 b | 3.5 b | 12.9 a | 3.3 ab | 1350 bc | 1135.0 b |

[1]Data within same column followed by the same letter are not significantly different (P = 0.05) according to Duncan's multiple-range test.
[2]Method of application: A = applied in moldboard plow furrow 10" deep spaced 8" apart 8 days before planting, B = injected 10" deep in row with single chisel 8 days before planting, C = applied in 12" band over row, rototilled 2" deep at plant.
[3]% sound mature kernel (SMK) determined from composit sample from four replications.
[4]Root-knot index based on rating of 0–10: 0 = no galling, 10 = 100% of roots and pods galled.
[5]White mold hits = number of hits per 50 ft row. One or more plants infected per ft of row is one hit.
[6]Stand = number of plants emerged per m of row.
[7]Vigor rating based on scale of 1–5: 1 = poor growth, 5 = excellent growth.

What is claimed is:

1. A nematocidal agricultural formulation for the control of nematodes consisting essentially of a D-limonene solvent and between 15% and 20% of chloropicrin, the percentage being by weight.

2. A method of controlling nematode infestation comprising applying to said nematodes or the habitate thereof a composition consisting essentially of a D-limonene solvent and between 15% and 20% by weight of chloropicrin.

* * * * *